US006343604B1

(12) United States Patent
Beall

(10) Patent No.: US 6,343,604 B1
(45) Date of Patent: Feb. 5, 2002

(54) PROTECTIVE NON OCCLUSIVE WOUND SHIELD

(76) Inventor: John Arthur Beall, 1016 S. Tracy Ave., Bozeman, MT (US) 59715

( * ) Notice: Subject to any disclaimer, the term of this patent is extended or adjusted under 35 U.S.C. 154(b) by 0 days.

(21) Appl. No.: 09/351,365

(22) Filed: Jul. 12, 1999

(51) Int. Cl.[7] .................................................. A61F 5/37
(52) U.S. Cl. ...................................... 128/846; 128/888
(58) Field of Search ................................. 128/846, 878, 128/879, 882, 888, 889; 602/41, 42, 43

(56) References Cited

U.S. PATENT DOCUMENTS

| | | | | |
|---|---|---|---|---|
| 2,443,481 A | * | 6/1948 | Sene ........................... 128/888 |
| 2,785,677 A | * | 3/1957 | Stumpf ........................ 128/888 |
| 4,023,569 A | * | 5/1977 | Warnecke .................... 128/888 |
| 4,134,399 A | * | 1/1979 | Halderson .................... 128/888 |

* cited by examiner

Primary Examiner—Michael A. Brown

(57) ABSTRACT

This device is a simple non occlusive protective WOUND SHIELD which protects most wounds without contacting the wound and consists of a single piece of convexly curved thermoplastic material forming a dome over the wound that said dome rests on a contiguous rim which is seated on the skin surrounding the wound and this said rim having several tabs attached for the purpose of securing the WOUND SHIELD to the skin surrounding the wound with roller adhesive tape or velcro tape and said dome having multiple perforations in its convexity to permit atmospheric air to circulate over the surface of the wound.

7 Claims, 2 Drawing Sheets

Sketch of forearm with SHIELD in place

1. Dome
2. Rim
3. Tag
4. Perforations
5. Adhesive Roll Tape

PROTECTIVE NON-OCCLUSIVE WOUND SHIELD

Drawings, Page 1

Frontal Perspective

Tangential Perspective

Cross section showing apex of SHIELD
¼" convexity of SHIELD

PROTECTIVE
NON- OCCLUSIVE WOUND SHIELD

Drawings, Page 2

Sketch of forearm with SHIELD in place

1. Dome
2. Rim
3. Tag
4. Perforations
5. Adhesive Roll Tape

PROTECTIVE NON OCCLUSIVE WOUND SHIELD

BACKGROUND OF THE INVENTION

The skin is the protective envelope of surface of the body against the superficial invasion of bacteria. Whenever the skin is assulted via abrasions (scuffing), punctures or lacerations, missles, surgical incisions etc. the opportunity for the invasion by bacteria inherent in the environment (clothing, earth contaminants etc.), foreign bodies and the adjacent skin itself, is presented. Only the ambient air has the least number of potential and opprotunistic bacterial invaders. These invasive bacteria thrive in an environment of body heat and moisture (blood and lymphatic fluid). Therefore it is important to expose the skin of a wound to the open air where bacteria do not thrive and a culture medium composed of blood and lymphatic fluid is not offered to the offending bacteria. Occluding the skin with the time honored occlusive bandages or dressings such as band aids (produced by Johnson and Johnson during the past 70 years) actually prevent the beneficial effect of the atmospheric air from deterring the growth of any bacteria that is already on the surrounding skin or carried on to the surface of the wound by clothing etc. These occlusive bandages stick to the wound and merely soak up lymphatic fluid and blood that may be present on the wound, thus providing a culture medium for bacterial growth and therefore shutting out the favorable effects of the ambient atmospheric air. For greater user (patient) comfort, wounds need to be protected from contact with the user's clothing and injury from unexpected bumping into fixtures of the environment etc. A protective wound shield of sturdy enough material the prevents accidental and additional injury to the wound would compliment the drying effects of the perforations that are in the embodiment of the non occlusive wound shield.

The pertinent prior art in wound shields include U.S. Pat. No. 2,443,481 which is a device for treatment of wounds invented by Sene. Stumpt discloses an Arched Protective Adhesive bandage in U.S. Pat. No. 2,785,677 Warnecke discloses in U.S. Pat. No. 4,023,569 a Device for Protection of Wounds, Halderson discloses in U.S. Pat. No. 4,134,399 a Skin Protection Device. Fryslie discloses in U.S. Pat. No. 4,677,666 a Protection Bandaging Device. Augustine discloses in U.S. Pat. No. 6,093,160 a Flexible Non Contact Wound device. Dadinis discloses in U.S. Pat. No. 6,107,563 a Flex Vented Dome Wound Protector Treatment Device.

SUMMARY OF THE INVENTION

The purpose of the non occlusive protective wound shield is an endeavor to offer to Health Care Professionals and the general public a wound protector device that could change currently accepted and almost uniformily used occlusive dressings to cover most wounds. The wound shield is a simple one piece of thermoplastic material with a central convexity dome that prevents contact with the wound, has perforations in the convexity, rests on a continuous ovoid rim that has several tags composite with a rim for the purpose of anchoring the device to the skin surrounding the wound with roller adhesive tape or VELCRO strips. The wound shield protects the wound from external trauma and deters bacterial contamination. The wound shield is inexpensive to produce in large numbers and is reusable. The concept of a non occlusive protective wound device has been patented by the seven cited references inventors but their designs are cumbersome and lack the refinement that the wound shield possesses. These refinements provide more ease of application to the wound and provide greater patient comfort,

Photographs 1 and illustrate the wound shield in a different color and anchored to a forearm.

DETAILED DESCRIPTION OF THE INVENTION

Figure 1:
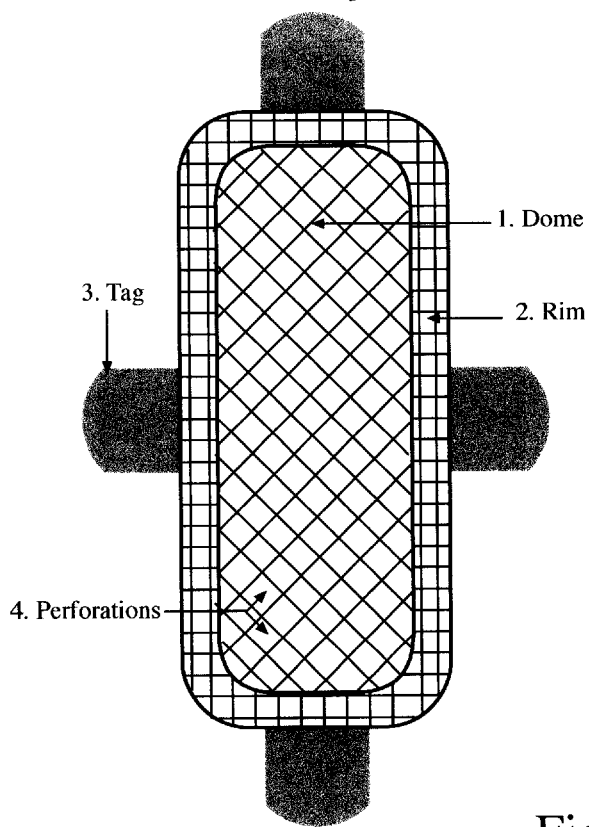
FIG. 1 is a frontal perspective of the wound shield.
Figure 2:
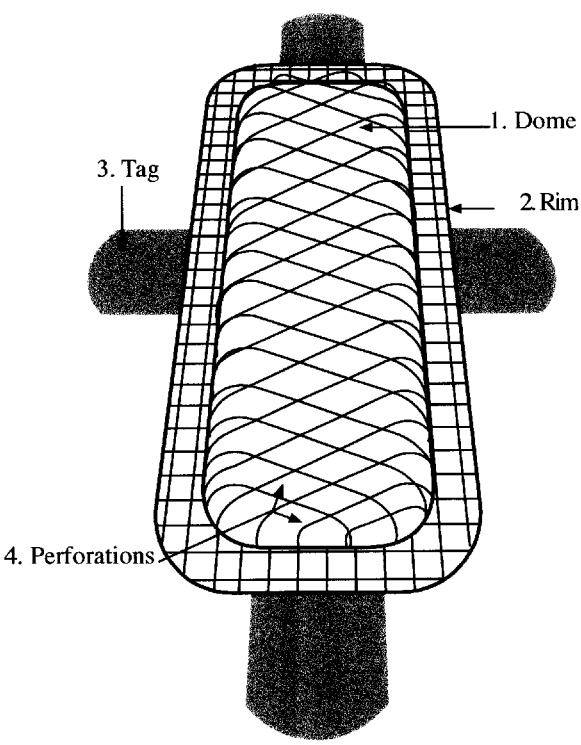
FIG. 2 is a tangential top view of the wound shield.
Figure 3:
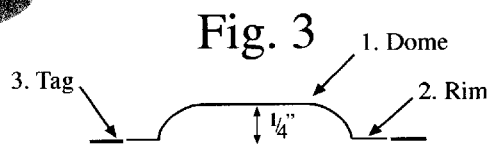
FIG. 3 is a cross sectional view of the wound shield.
Figure 4:
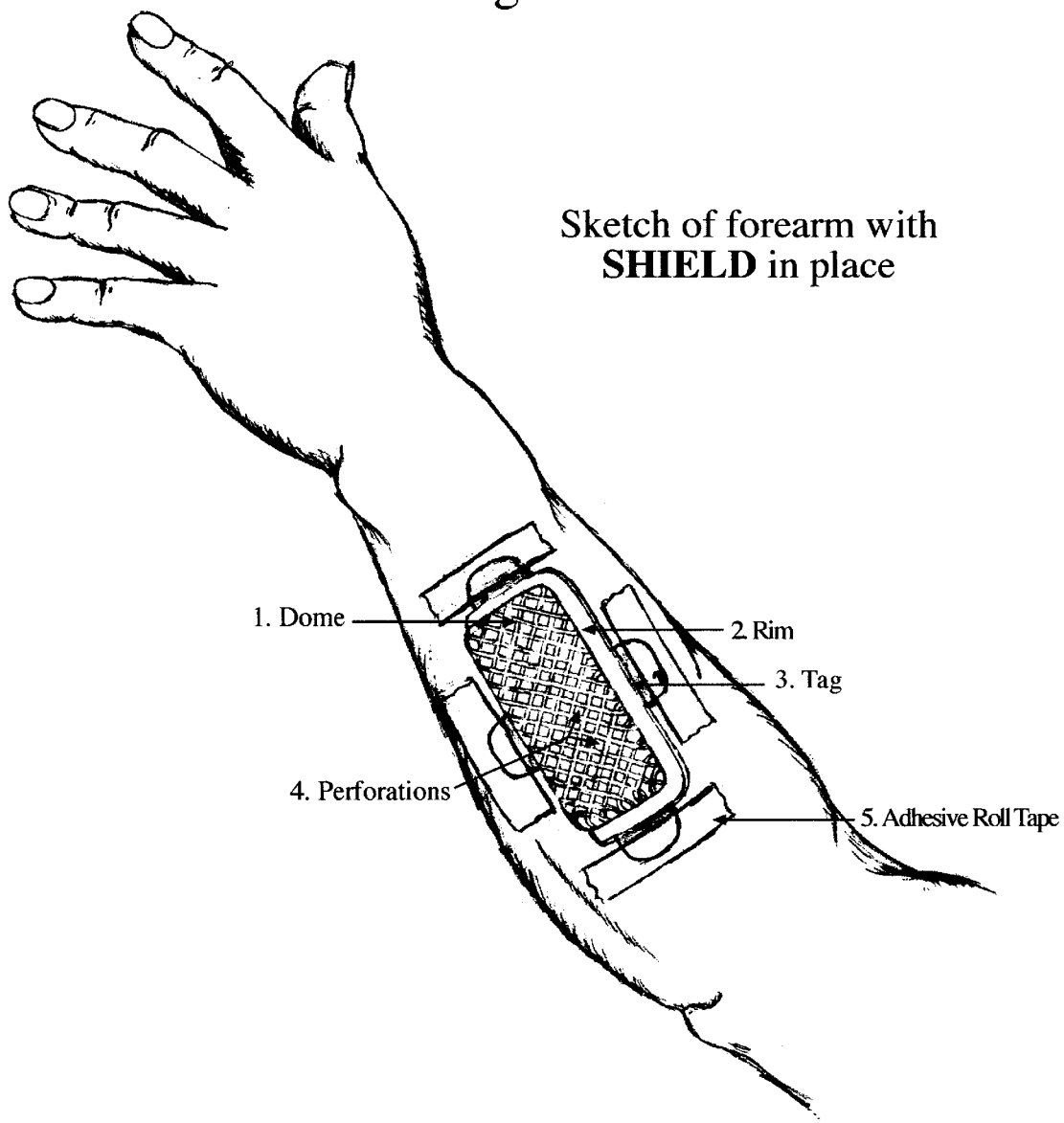
FIG. 4 is a top view of the wound shield attached to a forearm.

In FIGS. 1–2 the wound shield has a dome 1 that is convex shaped. The dome extends outwardly to a rim 2. There are tags 3 attached to the rim. The dome 1 has perforations 4 therein. FIG. 3 illustrates a cross-sectional view of the wound shield with the dome 1 and a rim 2 with contiguous attached tags 3. The apex of the dome of the shield is one fourth inches to three quarters inches in height. FIG. 4 illustrates the wound shield attached to a forearm with roller adhesive tape 5 that holds the shield to the user's forearm. Photographs 1 and 2 show a different color that the shield can be produced in. The dome is made of a thermoplastic material as produced by G.E. Plastic and Lavico Polymers. Thermoplastic materials are flexible enough to blend with the contour of most skin surfaces except over bony prominences where the wound shield could be trimmed with a scissors for better accommodation. The thermoplastic material could be pressure injected into suitably prepared molds. The perforations can vary in size from one sixteenth to one eighth inch in diameter. The shield is ovoid in shape. The tabs can be approximately three fourths inches wide and one inch in length. Either roller adhesive tape or VELCROstrips can be used to anchor the tabs of the wound shield to body skin surfaces.

What is claimed is:

1. A wound protection device comprising a convexly shaped dome having a flat rim extending around the peripheral of said convexly shaped dome, said convexly shaped dome made of a thermoplastic material, said convexly dome have perforations throughout the dome, a plurality of tags extending outwardly from said rim and adhesive strips attached over said tags to secure the convexly shaped dome to an appendage.

2. The wound protection device of claim 1, wherein said convexly shaped dome is oval shaped.

3. The wound protection device of claim 1, wherein the length of said tags is one inch and the width is three fourth of an inch.

4. The wound protection device of claim 1, wherein said thermoplastic material is polypropylene.

5. The wound protection device of claim 1, wherein said convexly shaped dome is made of different colors.

6. The wound protection device of claim 5, wherein said color of said convexly shaped dome is red.

7. The wound protection device of claim 5, where said color of said convexly shaped dome is white.

* * * * *